(12) United States Patent
Tjioe et al.

(10) Patent No.: US 7,094,927 B2
(45) Date of Patent: Aug. 22, 2006

(54) PROCESS FOR INCREASING THE CAPACITY OF A UREA PLANT

(75) Inventors: Tjay Tjien Tjioe, Sittard (NL); Jozef Hubert Meessen, Wijlre (NL)

(73) Assignee: DSM IP Assets B.V., (NL)

( * ) Notice: Subject to any disclaimer, the term of this patent is extended or adjusted under 35 U.S.C. 154(b) by 108 days.

(21) Appl. No.: 10/522,560

(22) PCT Filed: Jul. 10, 2003

(86) PCT No.: PCT/NL03/00509

§ 371 (c)(1),
(2), (4) Date: Jan. 27, 2005

(87) PCT Pub. No.: WO2004/011419

PCT Pub. Date: Feb. 5, 2004

(65) Prior Publication Data

US 2005/0288529 A1    Dec. 29, 2005

(30) Foreign Application Priority Data

Jul. 26, 2002  (NL) .................................. 1021176
Oct. 11, 2002  (NL) .................................. 1021637

(51) Int. Cl.
*C07C 273/12* (2006.01)
*C07C 273/04* (2006.01)
*C07D 251/60* (2006.01)

(52) U.S. Cl. ............................ 564/65; 564/66; 564/67; 564/70; 564/71; 564/72; 544/201; 422/129; 422/188; 422/200

(58) Field of Classification Search ............... 564/65, 564/66, 67, 70, 71, 72; 544/201; 422/129, 422/188, 200
See application file for complete search history.

(56) References Cited

FOREIGN PATENT DOCUMENTS

WO          98 08808        3/1998

OTHER PUBLICATIONS

International Search Report for PCT/NL2003/000509.

*Primary Examiner*—Peter O'Sullivan
(74) *Attorney, Agent, or Firm*—Mayer, Brown, Rowe & Maw LLP

(57) ABSTRACT

Process for increasing the capacity of a urea plant comprising a compression section, a high-pressure synthesis section, a urea recovery section, in which a urea melt is formed, and optionally a granulation section, the capacity of the urea plant being increased by the additional installation of a melamine plant and the urea melt from the urea recovery section of the urea plant being fed wholly or partly to the melamine plant and the residual gases from the melamine plant being returned wholly or partly to the high-pressure synthesis section and/or the urea recovery section of the urea plant.

20 Claims, 4 Drawing Sheets

FIGURE 1/4
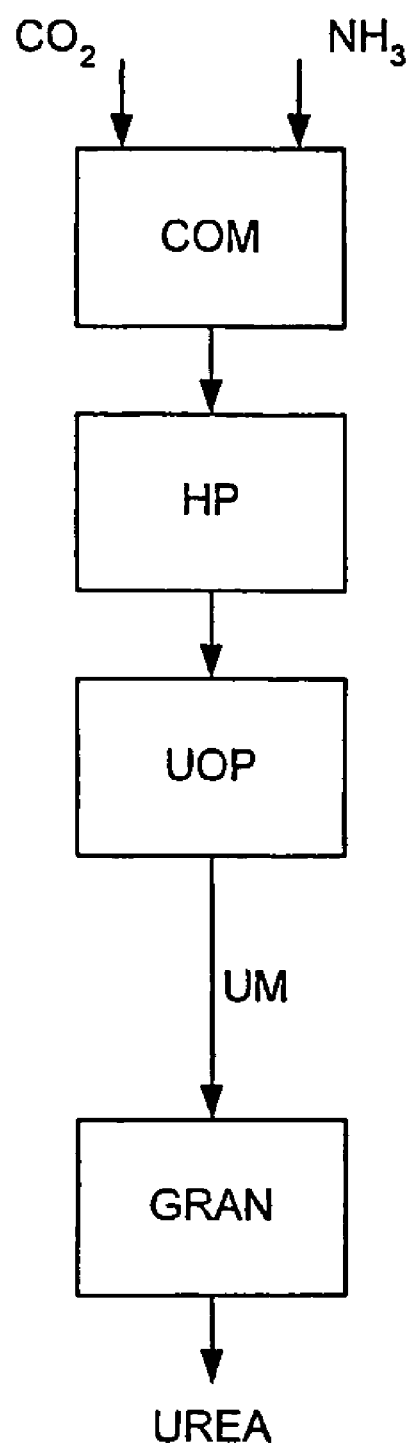

FIGURE 2/4
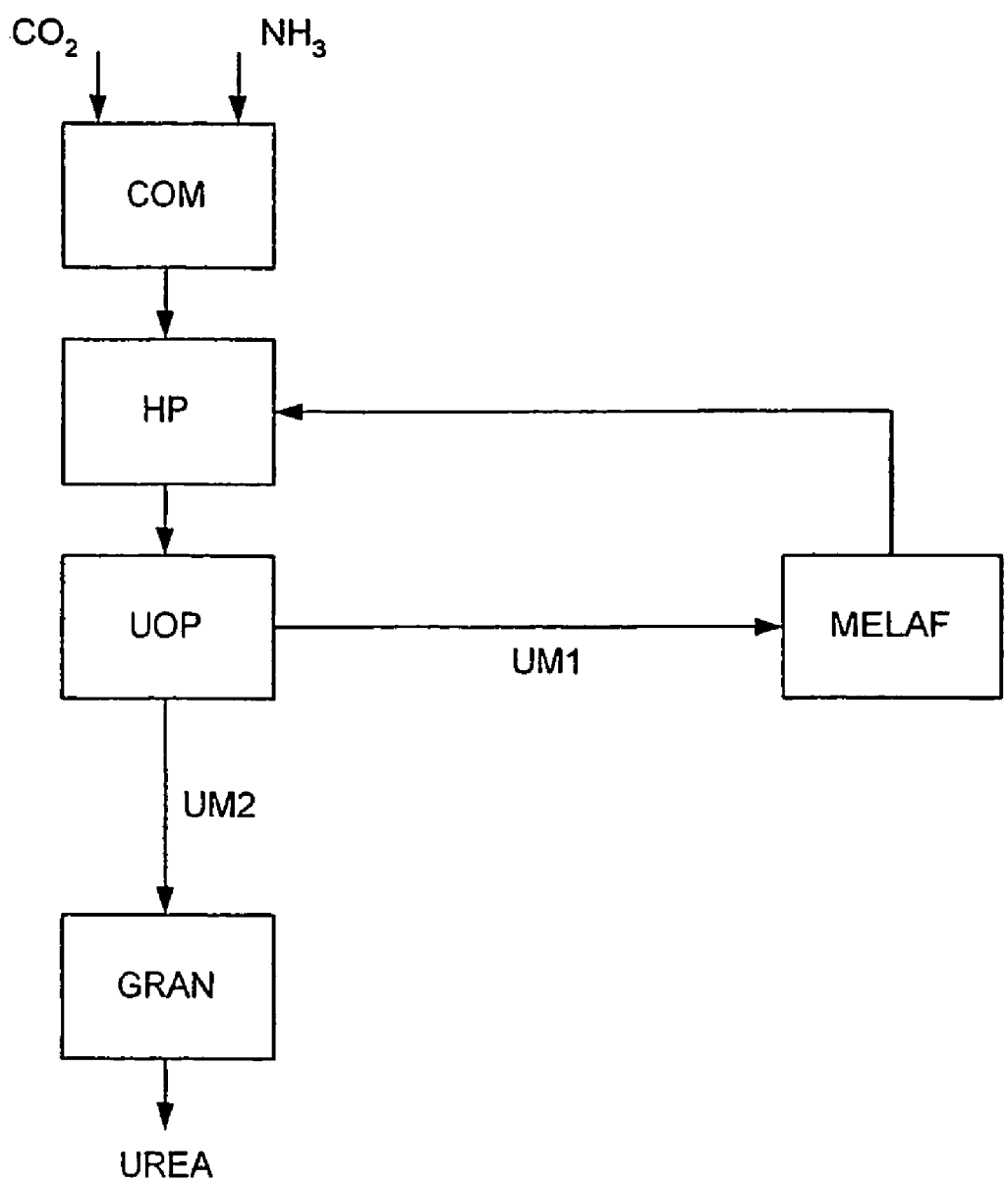

FIGURE 3/4
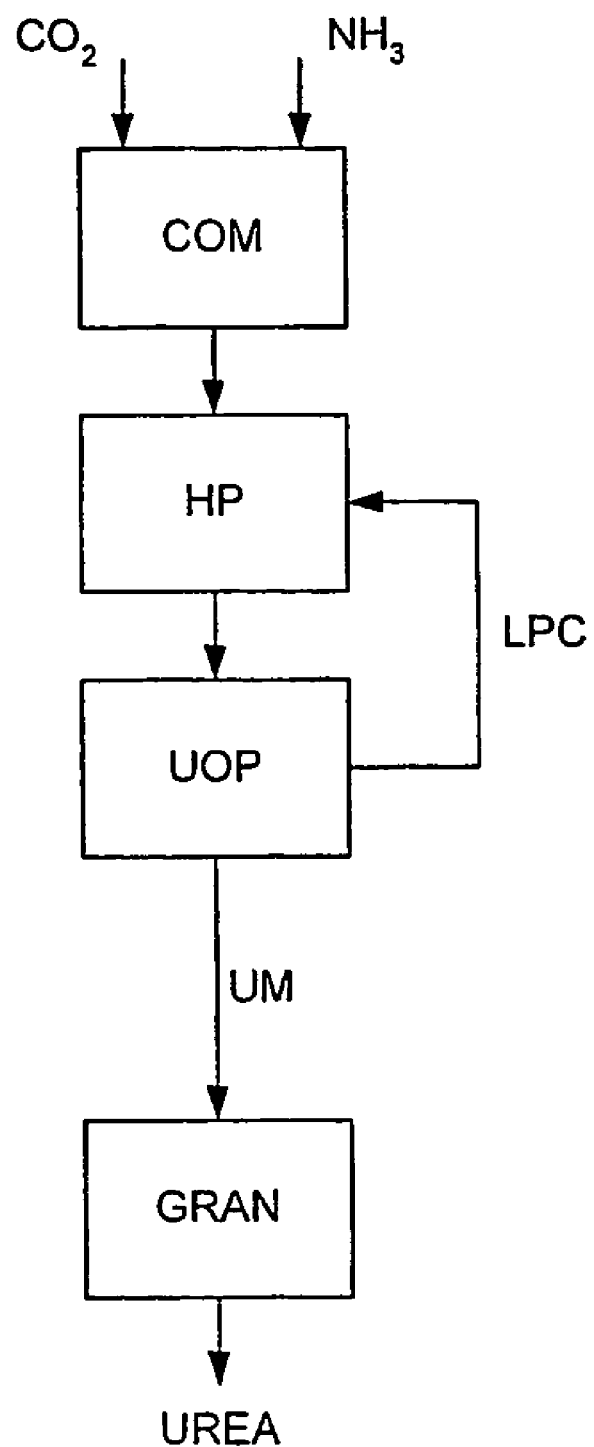

FIGURE 4/4
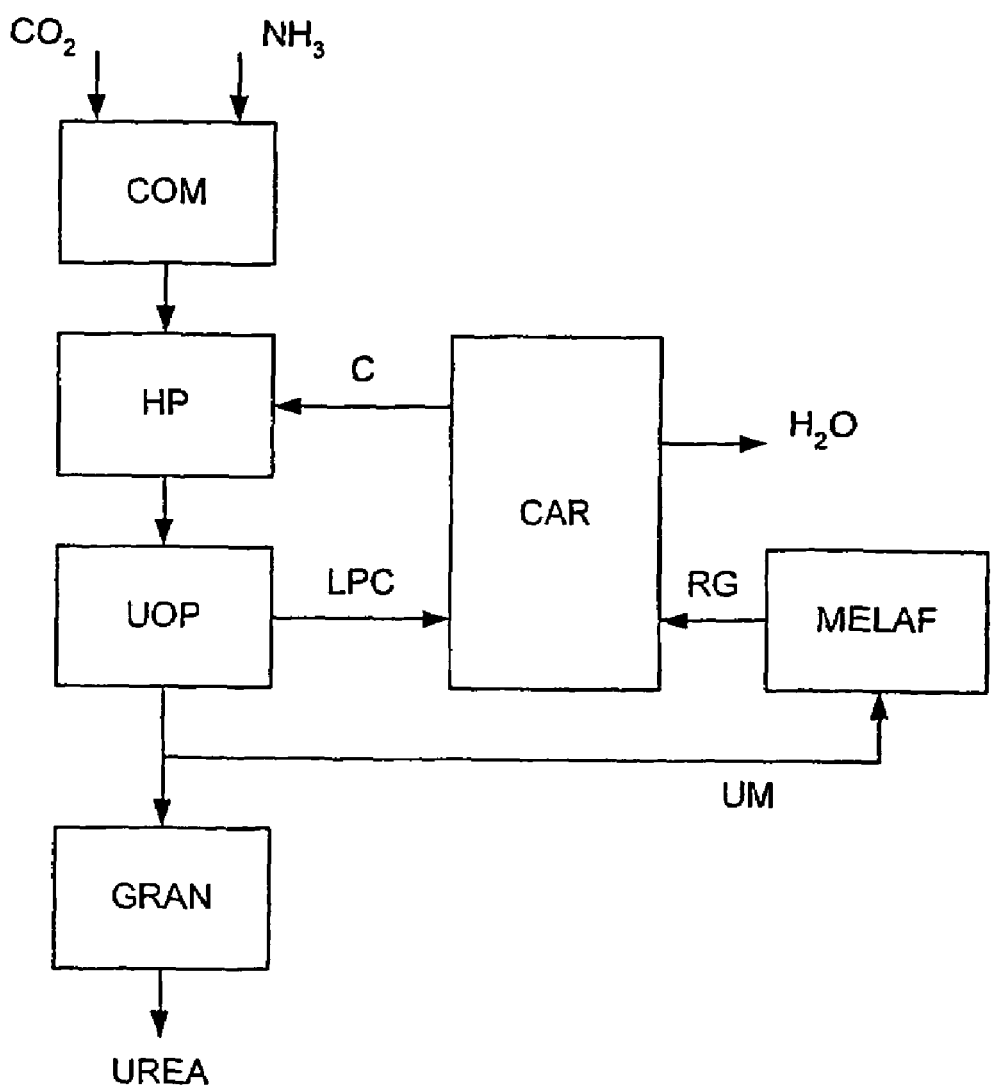

PROCESS FOR INCREASING THE CAPACITY OF A UREA PLANT

CROSS REFERENCE TO RELATED APPLICATION

This application is the National Phase of International Application PCT/NL2003/000509, filed Jul. 10, 2003, which designated the U.S., was published in the English language, and is incorporated by reference herein.

The invention relates to a process for increasing the capacity of a urea plant comprising a compression section, a high-pressure synthesis section, a urea recovery section, in which a urea melt is formed, and optionally a granulation section.

The capacity of a urea plant and of the sections thereof is here and hereinafter related to the quantity of urea that has been or can be synthesized. Various processes have been developed for increasing the capacity of a urea plant.

Examples of such processes are described for example in "Revamping urea plants", Nitrogen No. 157, 1985, pp. 37–42.

A disadvantage of the processes known until now is that it is necessary for increasing the capacity of a urea plant to increase the capacity of all sections of which a urea plant consists.

A process has now been developed for increasing the capacity of a urea plant which makes it possible to increase only the capacity of the high-pressure synthesis section and the urea recovery section.

This is achieved by the additional installation of a melamine plant, with the urea melt from the urea recovery section of the urea plant being fed wholly or partly to the melamine plant and the residual gases from the melamine plant being returned wholly or partly to the high-pressure synthesis section and/or the urea recovery section of the urea plant.

Because the residual gases are returned from the melamine plant to the high-pressure synthesis section and/or the urea recovery section of the urea plant, the urea production is increased without expanding the capacity of the compression section. The additionally produced urea is metered, in the form of a urea melt, to the melamine plant, so that there is no need to increase the capacity of the granulation section, either. An advantage of this process is that additionally produced urea is obtained while the capacity of only a part of the plant has been increased, so that the capacity expansion requires low investment costs.

If no granulation section is present in the urea plant, because the urea melt is recovered in a different way or is removed as such, this process is also advantageous, because in any case the compression section does not need to be expanded.

In the framework of this invention a urea plant may for example be a conventional urea plant, a urea stripping plant, or a combination of a conventional urea plant and a urea stripping plant.

For both types of urea plants the compression section forms the section in which carbon dioxide and/or ammonia are given a high pressure, the pressure in the high-pressure synthesis section.

A conventional urea plant is understood to mean a urea plant in which the decomposition of the ammonium carbamate that has not been converted into urea and the expulsion of the non-converted ammonia and carbon dioxide takes place at an essentially lower pressure than the pressure in the synthesis reactor itself. In a conventional urea plant the high-pressure synthesis section usually consists solely of the synthesis reactor in which a urea synthesis solution is formed, which is subsequently removed to the urea recovery section. In a conventional urea plant the synthesis reactor is generally operated at a temperature of 180–250° C. and a pressure of 15–40 MPa. After expansion, dissociation and condensation in the urea recovery section, the raw materials that have not been converted into urea in a conventional urea plant are separated at a pressure between 1.5 and 10 MPa and returned as an ammonium carbamate stream to the urea synthesis. Further, in a conventional urea plant ammonia and carbon dioxide are fed directly to the synthesis reactor. Subsequently in the urea recovery section at a lower pressure of usually 0.1–0.8 MPa almost all the residual non-converted ammonia and carbon dioxide are removed from the urea synthesis solution, yielding a solution of urea in water. This solution of urea in water is then converted at reduced pressure, by evaporation of water, into a concentrated urea melt. The separation of the urea-water mixture is sometimes effected by means of crystallization, generally instead of the said evaporation, after which the crystals are melted to form a urea melt. The urea melt can then optionally be processed further in a granulation section, with urea granules being obtained that have the desired particle size.

A urea stripping plant is understood to be a urea plant in which the expulsion of the ammonia and carbon dioxide that have not been converted into urea for the major part takes place at a pressure that is essentially virtually equal to the pressure in the synthesis reactor. In a urea stripping plant the synthesis reactor, the stripper and the carbamate condenser together usually form the high-pressure synthesis section.

The major part of the decomposition of non-converted ammonium carbamate and the expulsion of the excess ammonia takes place in a stripper, whether or not with a stripping gas being added. In a stripping process carbon dioxide and/or ammonia can be used as the stripping gas, before these components are fed to the synthesis reactor. It is also possible to apply "thermal stripping" here, which means that ammonium carbamate is decomposed exclusively by means of heat supply and the id ammonia and carbon dioxide that are present are removed from the urea solution. Stripping can be carried out in one or more steps. A process is known for example in which first exclusively thermal stripping is carried out, after which a $CO_2$ stripping step takes place with more heat being supplied. The gas stream released from the stripper, which contains ammonia and carbon dioxide, is optionally returned to the reactor via a high-pressure carbamate condenser.

The synthesis reactor in a urea stripping plant is generally operated at a temperature of 160–240° C. and preferably at a temperature of 170–220° C. The pressure in the synthesis reactor is 12–21 MPa and preferably 12.5–19.5 MPa.

Urea stripping processes are described in Ullmann's Encyclopaedia of Industrial Chemistry, Vol. A 27, fifth ed., pp. 344–350. Examples of urea stripping processes are the Stamicarbon® $CO_2$ stripping process, the ACES process, the IDR process and the Snamprogetti Self-Stripping Process.

Downstream of the stripper the stripped urea synthesis solution is expanded to lower pressures in one or more pressure stages in the urea recovery section and evaporated, with a concentrated urea melt being obtained and a low-pressure ammonium carbamate stream being returned to the high-pressure synthesis section. Depending on the process this ammonium carbamate can be recovered in a single process step or in several process steps operating at different pressures.

The urea melt is processed into granulate in the granulation section. Instead of in a granulation section the urea melt can also be processed into prills in a prilling tower.

The melamine plant that is added can be a plant according to a gas-phase process, but also according to a high-pressure process. A gas-phase process is a low-pressure process, in which the melamine reactor is operated at a pressure between 0.1 and 3 MPa. Melamine production processes are described for example in Ullmann's Encyclopaedia of Industrial Chemistry, Vol. A16, fifth ed., pp. 174–179.

Increasing the capacity in the high-pressure synthesis section and the urea recovery section in a urea plant can be accomplished in different ways depending on the technology of the original urea plant. Preferably the urea plant is a urea stripping plant.

The urea melt leaving the urea recovery section is fed wholly or partly to the melamine plant, where the molten urea, generally after a few pretreatments, is fed to the reactor.

In a melamine plant urea is converted into melamine according to the following reaction $$6CO(NH_2)_2 \rightarrow (NCNH_2)_3 + 3CO_2 + 6NH_3$$

The residual gases from the melamine process, principally carbon dioxide and ammonia gas, can be returned as such, but also as a carbamate-containing stream, to the urea plant. A carbamate-containing stream is a liquid stream that contains carbon dioxide and ammonia, with the gases continuing to react wholly or partly to form ammonium carbamate (herein also referred to as 'carbamate' for short) according to the following reaction.

$$2NH_3 + CO_2 \rightarrow H_2N-CO-ONH_4$$

The carbamate-containing stream normally contains water. The carbon dioxide, ammonia and carbamate are dissolved in the water. The water is usually present in the carbamate-containing stream to prevent crystallization of the carbamate.

The residual gases to be returned can also be split into a stream that is rich in carbon dioxide and a stream that is rich in ammonia before being returned to the urea plant. The advantage of such a splitting operation is that the different gas streams can be returned to different places in the urea plant. The stream that is rich in carbon dioxide can for example be fed to a stripper as the stripping gas, while the ammonia-rich stream is returned to the carbamate condenser. A part of the ammonia-rich stream can also be returned to the melamine plant, where it can be used in the production of melamine.

As a result of the supply of residual gases from the melamine plant, the residual gases can meet part of the $CO_2$ requirement in the high-pressure synthesis section of the urea plant. Relative to the total quantity of $CO_2$ fed to the urea plant, the $CO_2$ weight fraction coming from the melamine plant amounts to more than 5%, preferably more than 10%, more preferably more than 25%, and most preferably more than 40%. The weight fraction will usually be lower than 80%, more preferably lower than 70%, even more preferably lower than 60%. If the residual gases fed to the urea plant also contain $NH_3$, the combined $NH_3$ and $CO_2$ weight fraction coming from the melamine plant is more than 5%, preferably more than 10%, more preferably more than 25%, and most preferably more than 50% relative to the total quantity of $CO_2$ and $NH_3$ fed to the urea plant. The weight fraction will usually be lower than 80%, more preferably lower than 70%, most preferably lower than 60%.

The residual gases coming from a gas-phase melamine plant are usually condensed to form a water-rich carbamate-containing stream. This water-rich carbamate-containing stream must be brought to synthesis pressure and also the water content in this carbamate-containing stream must be reduced before the carbamate-containing stream can be returned to the urea plant. Below several embodiments are given as examples for the processing of the residual gases or of the water-rich carbamate-containing stream from a gas-phase melamine plant, it being noted that the invention is not restricted to said embodiments.

The water-rich carbamate-containing stream can for example be made water-poor by desorption, after which the desorbed gases, consisting mainly of carbon dioxide and ammonia, are subsequently condensed and metered by means of a pump to the high-pressure synthesis section of the urea plant.

The water-rich carbamate-containing stream can also first be brought to synthesis pressure and afterwards be stripped in a separate carbamate stripper. This stripping operation can be effected thermally, but also by supplying carbon dioxide and/or ammonia as the stripping gas. The gas stream, consisting mainly of carbon dioxide and ammonia, that leaves the carbamate stripper, is returned to the high-pressure synthesis section of the urea plant.

One way to recover the residual gases is the following; the residual gases are fed to one or a number of successive partial condensation and compression steps, combined with separation steps so as to reduce the water content of the residual gases. In addition, by stepwise increasing the pressure of the residual gases (optionally with interim partial condensation) to a pressure that is somewhat higher than the pressure in the high-pressure synthesis section of a urea plant, the resulting gas stream can be fed to the high-pressure synthesis section of the urea plant. The residual gases can for example be fed to a urea reactor, to a stripper, to a carbamate condenser or to lines between these.

In a preferred embodiment of the process the residual gases coming from the gas-phase melamine plant or the carbamate-containing stream are fed to the carbamate condenser or to a line that leads to the carbamate condenser.

It is also possible for the residual gases or the carbamate-containing stream to be fed to the urea recovery section, after which they can be returned to the high-pressure synthesis section together with the carbamate-containing stream from the urea recovery section. An advantage of this process is that there is no need to bring the residual gases to a high pressure, because the urea recovery section has a much lower pressure than the high-pressure synthesis section.

Preferably the water-rich carbamate-containing stream coming from the melamine plant and a carbamate-containing stream coming from the urea recovery section of the urea plant are recovered together and the resulting carbamate-containing stream is returned to the high-pressure synthesis section of the urea plant. This way, one recovery section will suffice and there is no need for two recovery sections: one for the recovery of the carbamate-containing stream from the urea plant and one for the recovery of the carbamate-containing stream from the melamine plant. For investment reasons this is advantageous.

Preferably the quantity of water in the carbamate-containing stream coming from a gas-phase melamine plant which is sent to the urea plant is lower than 40 wt. %, and in particular lower than 25 wt. %. The carbamate-containing stream which is sent to the urea plant preferably contains not less than 10 wt. % water, with special preference not less than 15 wt. % water, to prevent the formation of solids in the carbamate-containing stream.

The gas stream from a high-pressure melamine process, consisting principally of ammonia and carbon dioxide, can be fed to the urea recovery section and/or to the high-pressure synthesis section of a urea stripping plant and can there, for example, be fed to a urea reactor, to a stripper, to a carbamate condenser or to lines between them. Preferably, the gas stream coming from the melamine process is fed to the high-pressure synthesis section of a urea stripping plant. More preferably the gas stream coming from the melamine process is fed to the carbamate condenser or to a line that leads to the carbamate condenser.

The gas stream can also be fed to a pre-stripper installed between the reactor and the stripper or to a flash vessel installed between the stripper and the carbamate condenser. This pre-stripper is adiabatically operated.

The advantage of the use of the gas stream from a high-pressure melamine plant is that an almost water-free gas stream consisting of ammonia and carbon dioxide can be obtained for the urea stripping plant which, due to its almost water-free nature, provides for an improved efficiency in the urea plant compared to a urea plant that is fed with a water-rich carbamate stream from the gas-phase melamine plant. Furthermore, according to this process the gas stream coming from the melamine plant does not have to be subjected to a water removal step because the gas stream is already almost water-free and has a sufficiently high pressure. Further the extra heat released upon condensation of the gas stream from the high-pressure melamine plant can be used for additional steam production.

The pressure of the gas stream coming from the high-pressure melamine plant, principally consisting of ammonia and carbon dioxide, lies between 5 and 50 MPa, preferably between 8 and 30 MPa. In particular the pressure of the gas stream coming from the high-pressure melamine plant is 0–10 MPa and more in particular 0–2 MPa higher than the pressure in the urea reactor. The pressure of the gas stream from the melamine plant can first be lowered or increased before the stream is conveyed to the urea plant. The temperature of this gas stream lies between 135 and 275° C., preferably between 160 and 235° C.

In another embodiment the gas stream from a high-pressure melamine plant is first converted into a carbamate-containing stream by condensation and/or absorption in another carbamate-containing stream, before this stream is returned to the urea plant. The carbamate-containing stream from a high-pressure melamine plant that is returned to the urea plant preferably has a water content lower than 25 wt. % and in particular lower than 10 wt. %.

The condensation can be carried out in a condenser which is operated at a pressure which is substantially equal to the pressure in the melamine reactor. Preferably, the condenser is designed as a heat exchanger. In this case, a coolant is fed to the jacket side and the gas stream composed of carbon dioxide and ammonia is fed through the tube bundle. Since the condensation temperature in said condenser is between 100 and 230° C., vaporizing boiler feed water can be used as coolant, which has the additional advantage that the heat of condensation can profitably be used to produce low-pressure steam (0.3 to 1.0 MPa). If no profitable use is present in the plant surroundings for said low-pressure steam, cooling water can also, of course, be used as coolant.

Because the condensation takes place at a high pressure, higher temperatures can be reached here, so that the water content can be lower than in a carbamate-containing stream from a gas-phase melamine process without any risk of undesirable solids formation.

The $NH_3/CO_2$ molar ratio in the carbamate stream is preferably equal to or greater than 2 and preferably lower than 6, in particular lower than 4.

In one embodiment virtually all urea from the urea plant is fed to the melamine plant. This is understood to mean that, apart from the usual urea losses (in the waste water, to the air or at purification elements such as filters/adsorbents), no separate urea product stream leaves the urea plant, except to the melamine plant. In a special embodiment virtually all residual gases can be sent from the melamine plant to the urea plant. This is understood to mean that, apart from the usual residual gas losses, no separate residual gas stream leaves the melamine plant, except to the urea plant. If the residual gases are sent to the urea plant as a liquid carbamate stream, in one embodiment the carbamate stream can be increased in temperature by more than 20° C., preferably more than 40° C., to promote the conversion in the urea reactor. This heater can be located in the urea plant or in the melamine plant. The carbamate stream can be heated as such or after mixing with another carbamate stream from the urea plant. The temperature after heating of the liquid carbamate stream is lower than 250° C., preferably lower than 220° C.

The invention also relates to a urea plant comprising a compression section, a high-pressure synthesis section, a urea recovery section and optionally a granulation section, of which the high-pressure synthesis section and the urea recovery section have a higher capacity than the compression section and/or the optional granulation section. Preferably residual gases from a melamine plant are fed to the high-pressure synthesis section or the urea recovery section of the urea plant. Preferably the capacity of the high-pressure synthesis section and the urea recovery section in the urea plant is 5–50 wt % higher than the capacity of the compression section and/or the optional granulation section.

The invention will be elucidated hereinafter on the basis of FIGS. 1–4, without being restricted to these embodiments.

FIG. 1 shows a urea plant, according to the prior art, consisting of a compression section (COM) in which carbon dioxide ($CO_2$) and ammonia ($NH_3$) were brought to synthesis pressure. From the COM $CO_2$ and $NH_3$ were transferred to the high-pressure synthesis section (HP) where the urea was formed and subsequently the formed urea was recovered in the urea recovery section (UOP). After this the formed urea melt (UM) was fed to the granulation section (GRAN).

FIG. 2 shows a urea plant, according to the invention, consisting of a compression section (COM) in which carbon dioxide ($CO_2$) and ammonia ($NH_3$) were brought to synthesis pressure. From the COM $CO_2$ and $NH_3$ were transferred to the high-pressure synthesis section (HP) where the urea was formed and subsequently the formed urea was recovered in the urea recovery section (UOP). After this a part of the formed urea melt (UM1) was fed to the granulation section (GRAN) and another part (UM2) to the high-pressure melamine plant (MELAF). The residual gases (RG) from the MELAF were fed to the carbamate condenser in the HP.

The quantity of UM1 and UM2 together was higher than the quantity of UM produced in the urea plant according to the prior art described in FIG. 1.

FIG. 3 shows a urea plant, according to the prior art, consisting of a compression section (COM) in which carbon dioxide ($CO_2$) and ammonia ($NH_3$) were brought to synthesis pressure. From the COM $CO_2$ and $NH_3$ were transferred to the high-pressure synthesis section (HP) where the urea was formed and subsequently the formed urea was recovered in the urea recovery section (UOP). After this the formed urea melt (UM) was fed to the granulation section (GRAN) and a low-pressure carbamate stream (LPC) was returned from the UOP to the carbamate condenser in the HP. The LPC contained 30 wt. % water.

FIG. 4 shows a urea plant, according to the invention, consisting of a compression section (COM) in which carbon dioxide ($CO_2$) and ammonia ($NH_3$) were brought to synthesis pressure. From the COM $CO_2$ and $NH_3$ were transferred to the high-pressure synthesis section (HP) where the urea was formed and subsequently the formed urea was recovered in the urea recovery section (UOP). After this a part of the formed urea melt (UM1) was fed to the granulation section (GRAN) and another part (UM2) to the gas-phase melamine plant (MELAF). The residual gases (RG) from the MELAF were fed to a carbamate recovery section (CAR) where they were condensed with the low-pressure carbamate stream (LPC) from the UOP. The LPC contained 30 wt. % water. The carbamate stream (C) was concentrated and was returned with a water content of 20 wt. % to the carbamate condenser in the HP.

The quantity of UM1 and UM2 together was higher than the quantity of UM produced in the urea plant according to the prior art described in FIG. 3.

What is claimed is:

1. Process for increasing the capacity of a urea plant, comprising a compression section, a high-pressure synthesis section, a urea recovery section, in which a urea melt is formed, and optionally a granulation section, wherein the capacity of the urea plant is increased by the additional installation of a melamine plant, the urea melt from the urea recovery section of the urea plant being fed wholly or partly to the melamine plant and the residual gases from the melamine plant being returned wholly or partly to the high-pressure synthesis section and/or the urea recovery section of the urea plant.

2. Process according to claim 1, wherein the urea plant is a urea stripping plant.

3. Process according to claim 1, wherein the melamine plant is a gas-phase melamine plant.

4. Process according to claim 1, wherein the residual gases from the melamine plant are returned to the urea plant as a carbamate-containing stream.

5. Process according to, claim 1, in which the high-pressure synthesis section comprises a carbamate condenser, wherein the residual gases or the carbamate-containing stream are fed to the carbamate condenser or to a line that leads to the carbamate condenser.

6. Process according to claim 4, wherein the carbamate-containing stream coming from the melamine plant and a carbamate-containing stream coming from the urea plant are recovered together, before the carbamate-containing stream is returned to the urea plant.

7. Process according to claim 4, wherein the carbamate-containing stream that is returned to the urea plant contains 10–40 wt. % water.

8. Process according to claim 4, wherein the carbamate-containing stream that is returned to the urea plant contains 15–25 wt. % water.

9. Process according to claim 1, wherein the melamine plant is a high-pressure melamine plant.

10. Process according to claim 1, in which the high-pressure synthesis section comprises a carbamate condenser, wherein the residual gases are fed to the carbamate condenser or to a line that leads to the carbamate condenser.

11. Process according to claim 9, wherein the residual gases from the melamine plant are returned to the urea plant as a carbamate-containing stream, the water content of this carbamate stream being less than 25 wt. %.

12. Process according to claim 1, wherein the $CO_2$ weight fraction in the residual gases coming from the melamine plant is more than 5% relative to the total quantity of $CO_2$ fed to the urea plant.

13. Process according to claim 1, wherein the $CO_2$ and $NH_3$ weight fraction in the residual gases coming from the melamine plant is more than 5% relative to the total quantity of $CO_2$ and $NH_3$ fed to the urea plant.

14. Process according to claim 6, wherein the temperature of the carbamate-containing stream is increased by more than 20° C. before this stream is fed to the high-pressure synthesis section of the urea plant.

15. Process according to claim 1, wherein the residual gases to be returned are split into a stream that is rich in carbon dioxide and a stream that is rich in ammonia before being returned wholly or partly to the urea plant.

16. Urea plant comprising a compression section, a high-pressure synthesis section and a urea recovery section, wherein the high-pressure synthesis section and the urea recovery section have a higher capacity than the compression section.

17. Urea plant according to claim 16, wherein the capacity of the high-pressure synthesis section and the urea recovery section is 5–50 wt. % higher than the capacity of the compression section and/or the granulation section.

18. Process according to claim 2, wherein the melamine plant is a gas-phase melamine plant.

19. Process according to claim 5, wherein the carbamate-containing stream coming from the melamine plant and a carbamate-containing stream coming from the urea plant are recovered together, before the carbamate-containing stream is returned to the urea plant.

20. Process according to claim 2, wherein the melamine plant is a high-pressure melamine plant.

* * * * *